US005403598A

United States Patent [19]
Beck et al.

[11] Patent Number: 5,403,598
[45] Date of Patent: Apr. 4, 1995

[54] PHYSIOLOGICAL TEAR COMPOSITIONS AND METHODS FOR THEIR PREPARATION

[75] Inventors: Robert E. Beck; Haresh G. Bhagat, both of Fort Worth; Philip D. Gressel, Everman; Fred M. Killinger, Arlington, all of Tex.

[73] Assignee: Alcon Laboratories, Inc., Fort Worth, Tex.

[21] Appl. No.: 177,892

[22] Filed: Jan. 6, 1994

Related U.S. Application Data

[60] Division of Ser. No. 994,051, Dec. 16, 1992, abandoned, which is a continuation of Ser. No. 807,528, Dec. 13, 1991, abandoned.

[51] Int. Cl.$^6$ .............................................. A61K 33/00
[52] U.S. Cl. ..................................... 424/717; 424/700; 514/912
[58] Field of Search ............... 514/678, 679, 680, 681, 514/717, 912; 424/717, 700

[56] References Cited

U.S. PATENT DOCUMENTS

| | | | |
|---|---|---|---|
| 4,371,522 | 2/1983 | Gilbard | 424/153 |
| 4,443,432 | 4/1984 | Garabedian et al. | 424/127 |
| 4,550,022 | 10/1985 | Garabedian et al. | 424/127 |
| 4,775,531 | 10/1988 | Gilbard | 424/128 |
| 4,917,271 | 4/1990 | Kanner et al. | 222/189 |
| 5,025,957 | 6/1991 | Ranelletta et al. | 222/189 |

OTHER PUBLICATIONS

Bernal, D. L. and J. L. Ubels, "Quantitative Evaluation of the Corneal Epithelial Barrier: Effect of Artificial Tears and Preservatives," *Curr. Eye Res.*, 10(7):645–565 (1991).

Rismondo, V. et al. "Electrolyte Composition of Lacrimal Gland Fluid and Tears of Normal and Vitamin A–Deficient Rabbits," *CLAO Journal*, 15(3): 222–229 (1989).

*Drug Facts and Comparisons*, New York: J. B. Lippincott Co., 1989, pp. 504–504b.

Doughty, M. J., "Evidence for a Direct Effect of Bicarbonate on the Rabbit Corneal Stroma," *Optometry & Vision Sci.*, 68(9):687–698 (1989).

Edelhauser, H. et al., "Intraocular Irrigating Solution," *Arch. Ophthal.*, 93:648–657 (1975).

Bachman, W. G. and G. Wilson, "Essential Ions for Maintenance of the Corneal Epithelial Surface," *Invest. Ophthal. & Vis. Sci.*, 26:1484–1488 (1985).

Glasser et al., Chapter 17 of *The Cornea: Trans. of the World Congress on the Cornea III* (H. D. Cavanagh, ed.), New York: Raven Press Ltd., 1988.

*Primary Examiner*—Zohreh Fay
*Attorney, Agent, or Firm*—Jeffrey S. Schira; Julie J. Cheng

[57] ABSTRACT

Non-preserved physiological tear compositions comprise the ionic components of normal human tear film in substantially the same amounts and proportions. Novel methods of preparation of these compositions and novel packaging allow the maintenance of the bicarbonate concentration in these compositions.

10 Claims, No Drawings

PHYSIOLOGICAL TEAR COMPOSITIONS AND METHODS FOR THEIR PREPARATION

This is a divisional of U.S. patent application Ser. No. 07/994,051, filed Dec. 16, 1992, now abandoned, which is a continuation of U.S. patent application Ser. No. 07/807,528, filed Dec. 13, 1991, now abandoned.

BACKGROUND OF THE INVENTION

This invention relates generally to ophthalmic compositions. In particular, the present invention relates to artificial tear compositions comprising the ionic components of normal human tear film in substantially the same amounts and proportions, as well as to methods for their preparation and storage.

The compositions of the present invention are also useful as lubricating and cushioning agents for the eye after traumatic injury or surgery. The present invention also relates to a method of treating eyes by topically applying the formulations of the present invention when indicated for the relief of dry eye syndrome and when indicated to achieve the other effects mentioned above.

Dry eye syndrome and related ailments, including transitory discomforts, are well known in the scientific and patent literature. These ailments have generally been treated by topical administration of any of a number of ophthalmic compositions. The currently marketed artificial tear compositions are listed on pages 504–504b of *Drug Facts and Comparisons*, New York: J. B. Lippincott Co., 1989. In general, these compositions contain salts, buffers and viscosity agents (e.g., hydroxypropyl methylcellulose, polyvinyl alcohol, Carbopol ®, a carboxy vinyl polymer). Most artificial tear compositions additionally contain preservatives (e.g., benzalkonium chloride, Dymed ®, a biguanide, and Polyquad ®, a polymeric quaternary ammonium compound), although some recently introduced compositions are non-preserved.

It has recently been determined that preservatives and non-physiologic ions which may be present in artificial tear compositions may be detrimental to the corneal epithelium. See, for example, Bernal et al., *Current Eye Research*, 10(7):645–656 (1991). There have therefore been attempts to develop non-preserved artificial tear compositions containing physiological tear components. See, for example, U.S. Pat. No. 4,775,531 (Gilbard); however, these formulations are based on the composition of rabbit tears and it has now been documented that human tears, although having the same types of ions, have distinctly different ion concentrations. See Rismondo et al., in *The Contact Lens Association of Ophthalmologists*, 15(3):222–229 (1989). In addition, although Gilbard's compositions list bicarbonate as an ingredient, bicarbonate is quite labile, since it is in equilibrium with carbon dioxide, and could escape from solution in a relatively short time.

SUMMARY OF THE INVENTION

The compositions of the present invention are non-preserved compositions which contain the essential ionic components of normal human tear film in substantially the same amounts and proportions and which avoid some of the problems of known compositions. In addition, it has surprisingly been found that compositions containing bicarbonate are substantially more effective in treating dry eye syndrome and its related ailments, than currently available artificial tear preparations.

Further, the compositions of the present invention are prepared by an unique method which involves the use of $CO_2$ gas in order to retain bicarbonate in solution during preparation. The amount of bicarbonate dissolved in the solution depends on the components and conditions in the solution, as well as the conditions of the atmosphere surrounding the solution. An equilibrium is established which depends on these parameters, as described in the equation below:

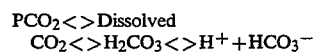
$$PCO_2 <> \text{Dissolved}$$
$$CO_2 <> H_2CO_3 <> H^+ + HCO_3^-$$

(where $PCO_2$ is the partial pressure of $CO_2$ above the solution). The bicarbonate concentration is maintained during storage by use of the novel packaging of the present invention, which creates a closed system in which an equilibrium between $CO_2$ and bicarbonate can be reached and maintained until the composition is to be utilized.

DETAILED DESCRIPTION OF THE INVENTION

In general, the ion components of the compositions of the present invention comprise: potassium at a concentration of between about 11 and about 25 millimoles per liter (mmol/l); calcium at a concentration of between about 0.2 and about 0.5 mmol/l; magnesium at a concentration of between about 0.15 and about 0.45 mmol/l; and bicarbonate at a concentration of between about 1 and about 36 mmol/l, preferably between about 6 and about 24 mmol/l. The compositions may additionally contain zinc at a concentration between about 0.005 and about 0.015 mmol/l. In a preferred composition of the present invention, the potassium ion concentration is about 17.4 mmol/l, the calcium ion concentration is about 0.36 mmol/l, the magnesium ion concentration is about 0.31 mmol/l and the bicarbonate concentration is about 11.9 mmol/l. As used throughout this application, all concentrations refer to final composition concentrations, unless otherwise stated.

It is preferred that the compositions of the present invention have certain ion ratios. In particular, it is preferred that: the molar concentration ratio of potassium to bicarbonate is between about 1:0.04 and about 1:3.27; the molar concentration ratio of calcium to magnesium is between about 1:0.3 and about 1:2.25; the molar concentration ratio of potassium to calcium is between about 1:0.008 and about 1:0.045; and the molar concentration ratio of bicarbonate to calcium is between about 1:0.0056 and about 1:0.5. Especially preferred are molar concentration ratios of: potassium to bicarbonate between about 1:0.24 and about 1:2.18; and bicarbonate to calcium between about 1:0.008 and about 1:0.08. Most preferred are the compositions of the present invention wherein the molar concentration ratio of potassium to bicarbonate is about 1:0.68, the molar concentration ratio calcium to magnesium is about 1:0.86, the molar concentration ratio of potassium to calcium is about 1:0.02 and the molar concentration ratio of bicarbonate to calcium is about 1:0.03.

The compositions of the present invention may additionally contain sodium chloride at a concentration between about 75 and about 154 mmol/l so that the osmolality is between about 200 and about 350 milliOsmoles/kilogram (mOsm/kg). It is preferred that the compositions have an osmolality of between about 260 and about 330 mOsm/kg. The compositions of the present invention will have a pH between about 5.0 and about 9.5. It is preferred that the compositions have a pH between about 5.5 and 8.5.

The compositions of the present invention may additionally contain mucomimetic polymers and lubricating agents for increased comfort and sustained duration in the eye. Examples of the above include: Dextran; cellulose derivatives, e.g., hydroxypropyl methylcellulose, hydroxyethyl cellulose, hydroxypropyl cellulose; polyvinyl pyrrolidone; and polyethylene glycols. In general, these polymers are present in the compositions of the present invention at a concentration between about 0.05 and about 5.0 percent by weight (wt %), preferably between about 0.1 and about 2.0 wt %.

The compositions of the present invention are prepared by dissolving or dispersing all of the ingredients in purified water in a pressure vessel. The components are mixed and the reactor heated to a suitable temperature for a time sufficient to achieve assured sterilization, according to common sterilization procedures. The mixture is then cooled to room temperature with mixing. In the alternative, a solution of bicarbonate which has previously been sterilized by filtration may be added at this stage. The pH of the composition is adjusted to the desired range (between 5.6 and 7.9) by use of sterile carbon dioxide and mixing the contents of the reactor. Sodium hydroxide and/or hydrochloric acid may additionally be used to adjust the pH of the mixture. The final product is then aseptically filled according to procedures known in the art.

In another alternative, all of the ingredients are dissolved or dispersed in purified water, followed by pH adjustment as described above. Sterilization may be accomplished either by filtration of the composition into a pressure vessel prior to the pH adjustment or by filtration of the composition directly into the filling machine after pH adjustment.

This method may also be used to prepare compositions containing other labile ingredients so that there is no significant loss of the labile ingredient from the composition. In general, the components are mixed and placed in a pressure reactor vessel. This vessel is then charged with a quantity of a gas with which the labile ingredient can establish an equilibrium. The quantity of gas added to the pressure reactor vessel must be sufficient to induce an equilibrium state between the gas and the labile ingredient within the closed system of the pressure reactor vessel. An example of another labile ingredient and its gas counterpart is ammonium ion and ammonia gas.

The packaging of the present invention comprises a material which is relatively non-permeable with respect to the gas contained in the composition. For example, if the gas is carbon dioxide, laminated foil or some high density plastics would be suitable packaging material. The final packaging of the compositions of the present invention may consist of multiple layers of packaging. The choice of material will in part depend on the desired product shelf life; i.e., the longer the desired shelf life, the less porous the material needs to be. The compositions of the present invention are preferably packaged in unit dose containers which are then sealed into laminated foil pouches. The manufacture and filling of such unit dose containers are known in the art (generally referred to as "form, fill and seal"). Multiple unit dose containers may be packaged in each laminated foil pouch.

Although it is preferred that the compositions be packaged in unit dose containers, it is understood that multidose non-preserved dispensing package systems could be used, so long as the packaging contains an appropriate barrier to prevent or reduce the escape of gas. For example, a packaging system consisting of laminate tubes utilizing dispensing tip assemblies such as those disclosed in U.S. Pat. No. 4,917,271 (Kanner et al.) and U.S. Pat. No. 5,025,957 (Ranalletta et al.), would be suitable packaging for the compositions of the present invention.

The compositions of the present invention are primarily intended for the relief of the symptoms of dry eye syndrome, particularly keratoconjunctivitis sicca. Symptoms include, without limitation, foreign body sensation, burning and hyperemia. In general, a dose of one or two drops of the present invention is administered once or more per day, although dosing may be less frequent, depending on the severity of the disease. Frequency of dosing is variably dependent upon severity; in severe cases, dosing may occur eight or more times per day.

EXAMPLE 1

Table 1, below, represents some preferred tear formulations of the present invention. For the sake of illustration, following are two of the preparation procedures used for Formulation A of Table 1.

In a reactor vessel, the sodium chloride, potassium chloride, calcium chloride, magnesium chloride, zinc chloride and Dextran 70 were dissolved in approximately 750 liters (l) of hot purified water, then hydroxypropyl methyl cellulose was dispersed into the solution. The dispersion was sterilized by heating to 250°–260° F. for 30 minutes, then cooled to room temperature to dissolve the hydroxypropyl methylcellulose. In a separate container, sodium bicarbonate was dissolved in 44 l of cool purified water; this solution was added to the reactor mixture through a sterilizing filter. Purified water was then added to the reactor mixture to bring the volume to 800 l. The pH of the resulting solution was approximately 8.1. The head space of the reactor vessel was pressurized to 15–20 pounds per square inch (psig) with carbon dioxide gas and the solution mixed for two hours. During this time, the pH of the solution decreased to approximately 6.0. After filling of the product into unit dose containers and sealing in foil pouches, the solution pH increased to 6.8–7.2 and then remained constant.

As a second illustration, a 50 l batch was prepared as above, except that the sodium bicarbonate was dissolved prior to heat sterilization of the batch. The pH of the solution increased to 9.4 during heating, but was reduced to 6.0 by mixing under carbon dioxide at 15 psig.

TABLE 1

| INGREDIENT | FORMULATIONS (WT. %) | | | | | | | | |
|---|---|---|---|---|---|---|---|---|---|
| | A | B | C | D | E | F | G | H | I |
| Dextran | 0.1 | 0.1 | 0.1 | 0.1 | 0.1 | 0.1 | 0.1 | 0.1 | 0.1 |
| Hydroxy- | 0.3 | 0.3 | 0.3 | 0.3 | 0.3 | 0.3 | 0.3 | 0.3 | 0.3 |

TABLE 1-continued

| Ingredient | | | | | | | | | |
|---|---|---|---|---|---|---|---|---|---|
| propyl-methyl-cellulose | | | | | | | | | |
| Sodium Chloride | QS to 280 mOsm/kg | QS to 230 mOsm/kg | QS to 310 mOsm/kg | QS to 260 mOsm/kg | QS to 275 mOsm/kg | QS to 245 mOsm/kg | QS to 290 mOsm/kg | QS to 310 mOsm/kg | QS to 290 mOsm/kg |
| Potassium Chloride | 0.13 | 0.186 | 0.13 | 0.082 | 0.082 | 0.186 | 0.13 | 0.13 | 0.13 |
| Calcium Chloride, × 2 H$_2$O | 0.0053 | 0.011 | 0.0053 | 0.0022 | 0.0022 | 0.0011 | 0.053 | 0.0053 | 0.0053 |
| Magnesium Chloride, × 6 H$_2$O | 0.0064 | 0.003 | 0.010 | 0.0064 | 0.003 | 0.010 | 0.0064 | 0.0064 | 0.0064 |
| Zinc Chloride | 0.00015 | 0.00015 | 0.00007 | 0.0002 | 0.00015 | 0.00007 | 0.00015 | 0.00015 | 0.00015 |
| Sodium Bicarbonate | 0.1 | 0.034 | 0.30 | 0.1 | 0.034 | 0.30 | 0.04 | 0.15 | 0.20 |
| Carbon Dioxide and/or NaOH and/or HCl | QS to pH | QS to pH | QS to pH | QS to pH | QS to pH | QS to pH | QS to pH | QS to pH | QS to pH |
| Purified Water | QS to 100 | QS to 100 | QS to 100 | QS to 100 | QS to 100 | QS to 100 | QS to 100 | QS to 100 | QS to 100 |

| | FORMULATIONS (WT. %) | | | | |
|---|---|---|---|---|---|
| INGREDIENT | J | K | L | M | N |
| Dextran | 0.1 | 0.1 | 0.1 | 0.1 | 0.1 |
| Hydroxypropyl-methylcellulose | 0.3 | 0.3 | 0.3 | 0.3 | 0.3 |
| Sodium Chloride | QS to 290 mOsm/kg | QS to 320 mOsm/kg | QS to 220 mOsm/kg | QS to 265 mOsm/kg | QS to 220 mOsm/kg |
| Potassium Chloride | 0.13 | 0.186 | 0.082 | 0.13 | 0.13 |
| Calcium Chloride, × 2 H$_2$O | 0.0053 | 0.0022 | 0.011 | 0.011 | 0.0022 |
| Magnesium Chloride, × 6 H$_2$O | 0.0064 | 0.010 | 0.003 | 0.0064 | 0.010 |
| Zinc Chloride | 0.00007 | 0.00015 | 0.00015 | 0.00015 | 0.00015 |
| Sodium Bicarbonate | 0.1 | 0.034 | 0.30 | 0.034 | 0.30 |
| Carbon Dioxide and/or NaOH and/or HCl | QS to pH | QS to pH | QS to pH | QS to pH | QS to pH |
| Purified Water | QS to 100 | QS to 100 | QS to 100 | QS to 100 | QS to 100 |

EXAMPLE 2

The compositions of the present invention were evaluated in an eight week open label, single center safety and efficacy clinical study (the "Study") with two groups of patients. Fourteen (14) patients (9 diagnosed with moderate dry eye and 5 diagnosed with severe dry eye) were enrolled in Group I and thirteen (13) patients (7 diagnosed with moderate dry eye and 6 diagnosed with severe dry eye) were enrolled in Group II. The two formulations listed in Table 2, below, were compared. Formulation 1 (Group I) and Formulation 2 (Group II) are identical, except that Formulation 1 contains bicarbonate, whereas Formulation 2 contains boric acid. Formulation 1 (Group I) is an example of a composition of the present invention.

TABLE 2

| INGREDIENT | FORMULATION 1 (WT. %) | FORMULATION 2 (WT. %) |
|---|---|---|
| Sodiun Chloride, USP | 0.66 | 0.66 |
| Potassium Chloride, USP | 0.13 | 0.13 |
| Calcium Chloride (× 2H$_2$O), USP | 0.0053 | 0.0053 |
| Magnesium Chloride (× 6H$_2$O), USP, AR | 0.0064 | 0.0064 |
| Zinc Chloride, USP | 0.00015 | 0.00015 |
| Sodium Bicarbonate, USP, AR | 0.1 + 20% xs | — |
| Boric Acid* | — | 0.35 |
| Dextran 70 | 0.1 | 0.1 |
| Hydroxypropyl Methylcellulose (2910) (E4M), USP | 0.3 | 0.3 |
| NaOH/HCl | QS to pH 7.7 | QS to pH 7.7 |

TABLE 2-continued

| INGREDIENT | FORMULATION 1 (WT. %) | FORMULATION 2 (WT. %) |
|---|---|---|
| Carbon Dioxide, USP | QS to pH 6 | — |
| Packaged product pH | 6.5–8.0 | 6.5–8.0 |
| Purified Water, USP | QS to 100 | QS to 100 |

*As a buffer

During the Study, the patients in both Group I and Group II were instructed to instill 1–2 drops of the test medication in each eye every 1–2 hours. Clinical visits were scheduled on Days 7, 28 and 56 (±3 days).

During each clinical visit, several tests were conducted in order to assess comfort and relief from symptoms, as well as to assess the effects of the compositions on the conjunctive and epithelial cells. These included: observations of ocular symptoms, e.g., foreign body sensation and discomfort, and observation of the ocular sign of rose bengal staining.

A. Ocular Symptoms

In observing ocular symptoms, the patients were asked to assess discomfort and foreign body sensations associated with instillation of the test formulations. Discomfort was defined as a positive sensation in the periocular (external eye) region and was graded on a scale of 0 to 3, wherein 0 indicated the absence of any positive sensation, and 3 indicated severe discomfort, e.g., exquisite ocular, periocular or radiating pain requiring analgesia and/or sedation. Foreign body sensation was also graded on a scale of 0 to 3, wherein 0 indicated the absence of foreign body sensation, and 3 indicated severe foreign body sensation similar to the sensation of a hot cinder in the eye, associated with constant tearing and blepharospasm. The results of the ocular symptom observations are summarized in the following Table 3.

TABLE 3

| | | FORMULATION 1 (n = 14) | | | | | |
|---|---|---|---|---|---|---|---|
| | | RIGHT EYE | | | LEFT EYE | | |
| SYMPTOM | DAY | IMPROVED | UNCHANGED | WORSE | IMPROVED | UNCHANGED | |
| Discomfort | 7 | 42.9 | 57.1 | ND | 42.9 | 57.1 | |
| (from | 28 | 71.4 | 21.4 | 7.1 | 71.4 | 28.6 | |
| baseline) | 56 | 85.7 | 7.1 | 7.1 | 85.7 | 14.3 | |
| Foreign | 7 | 50.0 | 50.0 | ND | 42.9 | 57.1 | |
| Body | 28 | 71.4 | 21.4 | 7.1 | 71.4 | 28.6 | |
| Sensation | 56 | 78.6 | 21.4 | ND | 78.6 | 21.4 | |

| | | FORMULATION 2 (n = 13) | | | | | |
|---|---|---|---|---|---|---|---|
| | | RIGHT EYE | | | LEFT EYE | | |
| SYMPTOM | DAY | IMPROVED | UNCHANGED | WORSE | IMPROVED | UNCHANGED | WORSE |
| Discomfort | 7 | 38.5 | 53.8 | ND | 38.5 | 46.2 | 7.7 |
| (from | 28 | 53.8 | 30.8 | ND | 46.2 | 38.5 | ND |
| baseline) | 56 | 38.5 | 38.5 | ND | 38.5 | 38.5 | ND |
| Foreign | 7 | 30.8 | 61.5 | ND | 38.5 | 53.8 | ND |
| Body | 28 | 15.4 | 61.5 | 7.7 | 23.1 | 53.8 | 7.7 |
| Sensation | 56 | 30.8 | 38.5 | 7.7 | 30.8 | 38.5 | 7.7 |

The results indicate that Formulation 1 (with bicarbonate) was more effective in relieving the patients' ocular foreign body sensation than Formulation 2 (without bicarbonate). Both formulations were statistically equivalent in the characteristic of relieving ocular discomfort. In Formulation 1, however, the majority of the patients demonstrated improvement in these two symptoms by the end of the study. Since the dry eye condition is characteristic of very bothersome symptoms which impact the patient's "quality of life," relieving these symptoms is very much desired.

B. Ocular Sign: Rose Bengal Staining

Rose bengal staining was used as an objective test to determine the extent of damage to the superficial corneal and conjunctival cells in dry eye syndrome. A normal eye exhibits little to no staining. This test is the single most objective clinical sign available to gauge clinical improvement in dry eye syndrome when assessing the efficacy of a treatment.

For each patient, five microliters ($\mu l$) of 1% rose bengal vita stain was placed into the inferior fornix of each eye and the patient instructed to blink several times and roll their eyes around. Each eye was then examined by slit lamp, using a green filtered light. The degree of staining was separately recorded for each of the temporal conjunctiva (outer portion), the cornea and the nasal conjunctiva (inner portion) on a scale of 0 to 3. The separate scores were then added to obtain the total score for each eye (maximum score of 9). The results of the rose bengal staining are summarized in the following Table 4.

TABLE 4

| | GROUP I (n = 14) | | | | | |
|---|---|---|---|---|---|---|
| | RIGHT EYE | | | LEFT EYE | | |
| DAY | IMPROVED | UNCHANGED | WORSE | IMPROVED | UNCHANGED | WORSE |
| 7 | 78.6 | 21.4 | ND | 71.4 | 14.3 | 14.3 |
| 28 | 71.4 | 14.3 | 14.3 | 78.6 | 14.3 | 7.1 |
| 56 | 78.6 | 7.1 | 14.3 | 78.6 | 14.3 | 7.1 |

| | GROUP II (n = 14) | | | | | |
|---|---|---|---|---|---|---|
| | RIGHT EYE | | | LEFT EYE | | |
| DAY | IMPROVED | UNCHANGED | WORSE | IMPROVED | UNCHANGED | WORSE |
| 7 | 53.8 | 23.1 | 15.4 | 69.2 | 15.4 | 7.7 |
| 28 | 61.5 | ND | 23.1 | 46.2 | 15.4 | 23.1 |

TABLE 4-continued

| 56 | 46.2 | 7.7 | 23.1 | 46.2 | 15.4 | 15.4 |

The results indicate that Formulation I (with bicarbonate), in particular, provided significant improvement in epithelial corneal and conjunctival cells at all three visits when compared to baseline rose bengal staining readings. This indicates that Formulation 1 is effective in improving the dry eye condition. Formulation 2 (without bicarbonate) also had a significant improving effect seven days after initiating therapy.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of preparing a composition containing bicarbonate, wherein there is no significant loss of the bicarbonate from the composition, said method comprising the steps of:
   a) mixing the composition ingredients in a suitable vessel;
   b) placing the composition in a pressure reactor vessel;
   c) charging the pressure reactor vessel with a quantity of carbon dioxide gas with which the bicarbonate can establish an equilibrium, wherein the quantity of gas is sufficient to induce a desired equilibrium state between the carbon dioxide gas and the bicarbonate within the closed system of the pressure reactor vessel; and
   d) mixing the contents of the pressure reactor vessel for a period of time sufficient to induce the desired equilibrium state between the carbon dioxide gas and the bicarbonate.

2. The method of claim 1, wherein the suitable vessel for mixing the composition ingredients is the pressure reactor vessel.

3. The method of claim 1, further comprising transferring the contents of the pressure reactor vessel into means for storage of the composition without significant loss of the bicarbonate.

4. The method of claim 3, wherein the means for storage of the composition comprises a container for the composition which is substantially impermeable to the carbon dioxide gas contained therein.

5. The method of claim 3, wherein the means for storage of the composition comprises a laminated foil pouch.

6. A method of preparing an ophthalmic composition containing bicarbonate, wherein there is no significant loss of the bicarbonate from the composition, said method comprising the steps of:
   a) mixing the composition ingredients in a suitable vessel;
   b) placing the composition in a pressure reactor vessel;
   c) charging the pressure reactor vessel with a quantity of carbon dioxide gas sufficient to induce a desired equilibrium state between the carbon dioxide and the dissolved bicarbonate within the closed system of the pressure reactor vessel; and
   d) mixing the contents of the pressure reactor vessel for a period of time sufficient to induce an equilibrium state between the carbon dioxide and the bicarbonate at a pH between 5.6. and 7.9.

7. The method of claim 6, wherein the suitable vessel for mixing the composition ingredients is the pressure reactor vessel.

8. The method of claim 6, further comprising transferring the contents of the pressure reactor vessel into means for storage of the composition without significant loss of bicarbonate.

9. The method of claim 8, wherein the means for storage of the composition comprises a container for the composition which is substantially impermeable to the carbon dioxide gas contained therein.

10. The method of claim 9, wherein the means for storage of the composition comprises a laminated foil pouch.

* * * * *